United States Patent
Chaptinel et al.

(10) Patent No.: US 11,147,455 B2
(45) Date of Patent: Oct. 19, 2021

(54) INTERACTIVE DATA ACQUISITION AND RECONSTRUCTION BY A MAGNETIC RESONANCE SYSTEM

(71) Applicants: Jérôme Chaptinel, Lausanne (CH); Tobias Kober, Lausanne (CH); Davide Piccini, Prilly (CH); Peter Speier, Erlangen (DE); Matthias Stuber, Lausanne (CH); Jérôme Yerly, Charmey (CH)

(72) Inventors: Jérôme Chaptinel, Lausanne (CH); Tobias Kober, Lausanne (CH); Davide Piccini, Prilly (CH); Peter Speier, Erlangen (DE); Matthias Stuber, Lausanne (CH); Jérôme Yerly, Charmey (CH)

(73) Assignees: CENTRE HOSPITALIER UNIVERSITAIRE VAUDOIS, Lausanne (CH); SIEMENS HEALTHCARE GMBH, Erlangen (DE)

( * ) Notice: Subject to any disclaimer, the term of this patent is extended or adjusted under 35 U.S.C. 154(b) by 350 days.

(21) Appl. No.: 15/944,635

(22) Filed: Apr. 3, 2018

(65) Prior Publication Data
US 2018/0289262 A1 Oct. 11, 2018

(30) Foreign Application Priority Data
Apr. 7, 2017 (EP) .................................. 17165537

(51) Int. Cl.
*A61B 5/00* (2006.01)
*G06T 11/00* (2006.01)
(Continued)

(52) U.S. Cl.
CPC .......... *A61B 5/0044* (2013.01); *A61B 5/0073* (2013.01); *A61B 5/055* (2013.01);
(Continued)

(58) Field of Classification Search
CPC ..... A61B 5/0044; A61B 5/055; A61B 5/7207; A61B 5/0073; A61B 5/4343;
(Continued)

(56) References Cited

U.S. PATENT DOCUMENTS 4,781,200 A * 11/1988 Baker ................ A61B 5/02411
600/483
2015/0226824 A1* 8/2015 Grimm ................ A61M 5/007
600/420
(Continued)

FOREIGN PATENT DOCUMENTS

DE 102014202513 A1 8/2015

OTHER PUBLICATIONS

Jerome Yerly et al.: "Coronary endothelial function assessment using self-gated cardiac eine MRI and k-t sparse SENSE" Coronary Endothelial Function Assessment Using Self-Gated Cardiac Cine MRI Magnetic Resonance in Medicine., Bd. 76, Nr. 5, pp. 1443-1454, 2015. (Year: 2015).*
(Continued)

*Primary Examiner* — Christopher Koharski
*Assistant Examiner* — Kaitlyn E Selmer
(74) *Attorney, Agent, or Firm* — Lempia Summerfield Katz LLC

(57) ABSTRACT

The disclosure relates to a method for the interactive acquisition of data from an object under investigation by a magnetic resonance system. The data is acquired from the object under investigation with the magnetic resonance system and images are automatically reconstructed and displayed in real time based on the data. A time interval is
(Continued)

determined during which a predetermined condition is met in the images. Quality images are automatically reconstructed based on the data acquired within the time interval. The temporal resolution during reconstruction of the quality images is higher than the temporal resolution during reconstruction of the images.

19 Claims, 3 Drawing Sheets

(51) Int. Cl.
 *A61B 5/055* (2006.01)
 *G01R 33/48* (2006.01)
(52) U.S. Cl.
 CPC .......... *A61B 5/4343* (2013.01); *A61B 5/7207* (2013.01); *G06T 11/003* (2013.01); *A61B 2503/02* (2013.01); *G01R 33/4824* (2013.01); *G06T 2207/10088* (2013.01)
(58) Field of Classification Search
 CPC .............. A61B 2503/02; G06T 11/003; G06T 2207/10088; G01R 33/4824; G01R 33/5608; G01R 33/5611
 See application file for complete search history.

(56) References Cited

U.S. PATENT DOCUMENTS

| | | | | |
|---|---|---|---|---|
| 2015/0342496 | A1* | 12/2015 | Greiser | A61B 5/02055 600/420 |
| 2015/0374237 | A1* | 12/2015 | Hu | A61B 5/7285 600/413 |
| 2016/0058363 | A1* | 3/2016 | Hayes-Gill | A61B 5/6804 600/588 |
| 2017/0307711 | A1* | 10/2017 | Wundrak | G01R 33/56518 |

OTHER PUBLICATIONS

Jerome Chaptinel et al.: "A Golden-Angle Acquisition Coupled with k-t Sparse SENSE Reconstruction for Fetal Self Retro-Gated Cine Cardiac MRI: an In Vivo Feasibility Study", Journal of the International Society for Magnetic Resonance in Medicine, ISMRM; Nr. 459, 2016. (Year: 2016).*

Jerome Yerly et al. "Coronary endothelial function assessment using self-gated cardiac cine MRI and k-t Sparse SENSE", 2015 (Year: 2015).*

Jerome Chaptinel et al. "A Golden-Angle Acquisition Coupled with k-t Sparse SENSE Reconstruction for Fetal Self Retro-Gated Cine Cardiac MRI: an In Vivo Feasibility Study" 2016 (Year: 2016).*

European Search Report for European Patent Application No. 17165537.6, dated Oct. 11, 2017.

B. Dale et al.: "A Rapid Look-Up Table Method for Reconstructing MR Images from Arbitrary K-Space Trajectories", IEEE Transactions on Medical Imaging, vol. 20, No. 3, Mar. 2001, pp. 207-217; 2001.

Van Amerom J. et al.: "Fetal cardiac cine imaging from motion-corrected super-resolution reconstruction of highly-accelerated real-time MRI", in: ISMRM, vol. 24, p. 458, 2016.

Votino C. et al.: "Magnetic resonance imaging in the normal fetal heart and in congenital heart disease", in: Ultrasound Obstet Gynecol; vol. 39, pp. 322-329, 2012.

Winkelmann S. et al.; "An Optimal Radial Profile Order Based on the Golden Ratio for Time-Resolved MRI"; IEEE Transactions on Medical Imaging 2007; vol. 26; No. 1; pp. 68-76, 2007.

McVeigh E. et al.: "Real-time, Interactive MRI for Cardiovascular Interventions", in: Academic Radiology, vol. 12, No. 9, Sep. 2005.

Haris K. et al.: "Fetal Cardiac MRI with self-gated iGRASP", in: ISMRM2016, vol. 24, p. 3104.

Jerome Chaptinel et al.: "A Golden-Angle Acquisition Coupled with k-t Sparse SENSE Reconstruction for Fetal Self Retro-Gated Cine Cardiac MRI: an In Vivo Feasibility Study", Journal of the International Society for Magnetic Resonance in Medicine, ISMRM; Nr. 459, 2016.

Hansen M. S. et al: "Retrospective reconstruction of high temporal resolution cine images from real-time MRI using iterative motion correction", Magnetic Resonance in Medicine., Bd. 68, Nr. 3, pp. 741-750, 2011.

Jerome Yerly et al: "Coronary endothelial function assessment using self-gated cardiac eine MRI and k-t sparse SENSE" Coronary Endothelial Function Assessment Using Self-Gated Cardiac Cine MRI Magnetic Resonance in Medicine., Bd. 76, Nr. 5, pp. 1443-1454, 2015.

Wielandner A. et al.: "Potential of magnetic resonance for imaging the fetal heart", in: Seminars in Fetal & Neonatal Medicine, vol. 18, pp. 286-297, 2013.

* cited by examiner

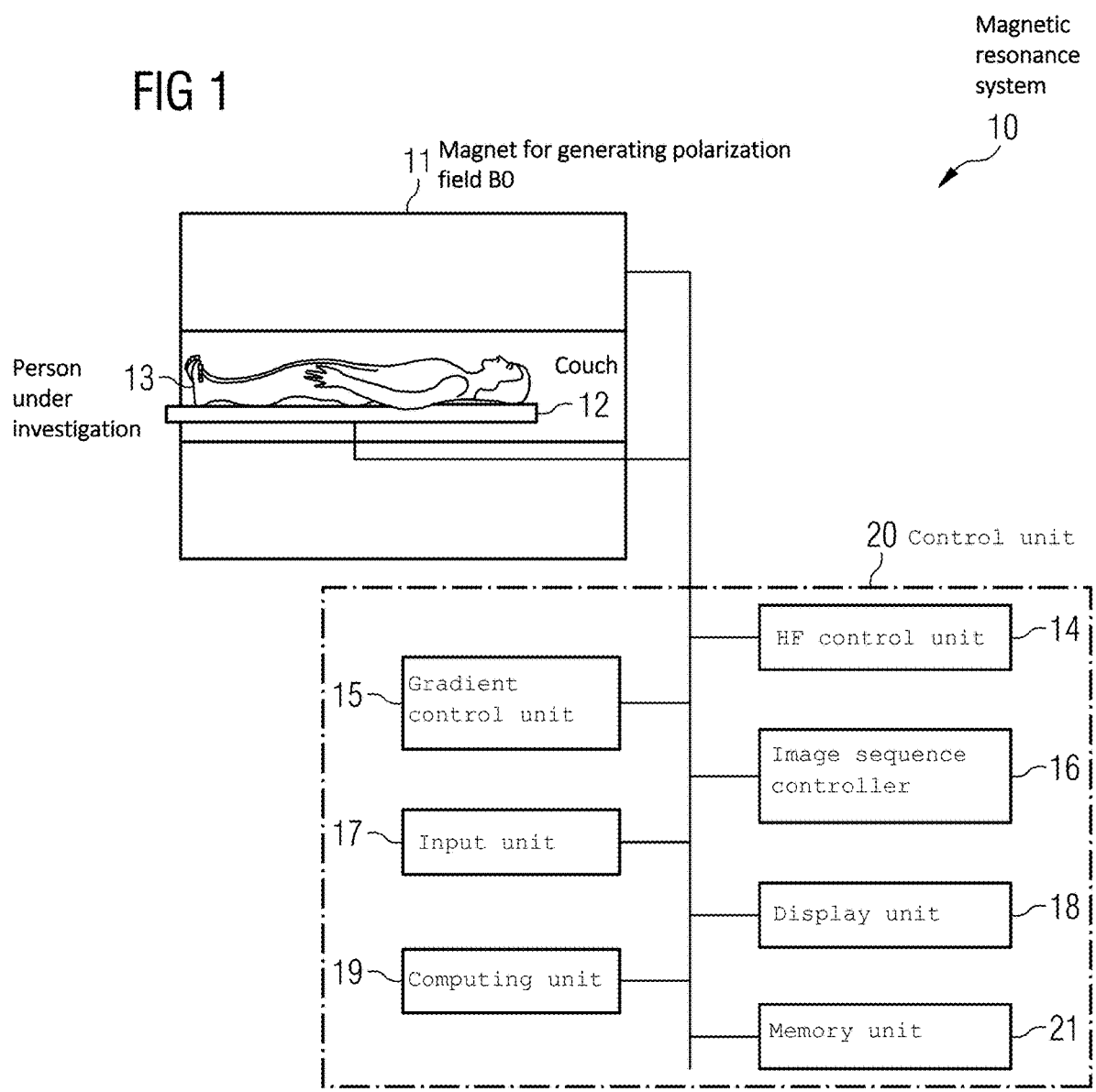

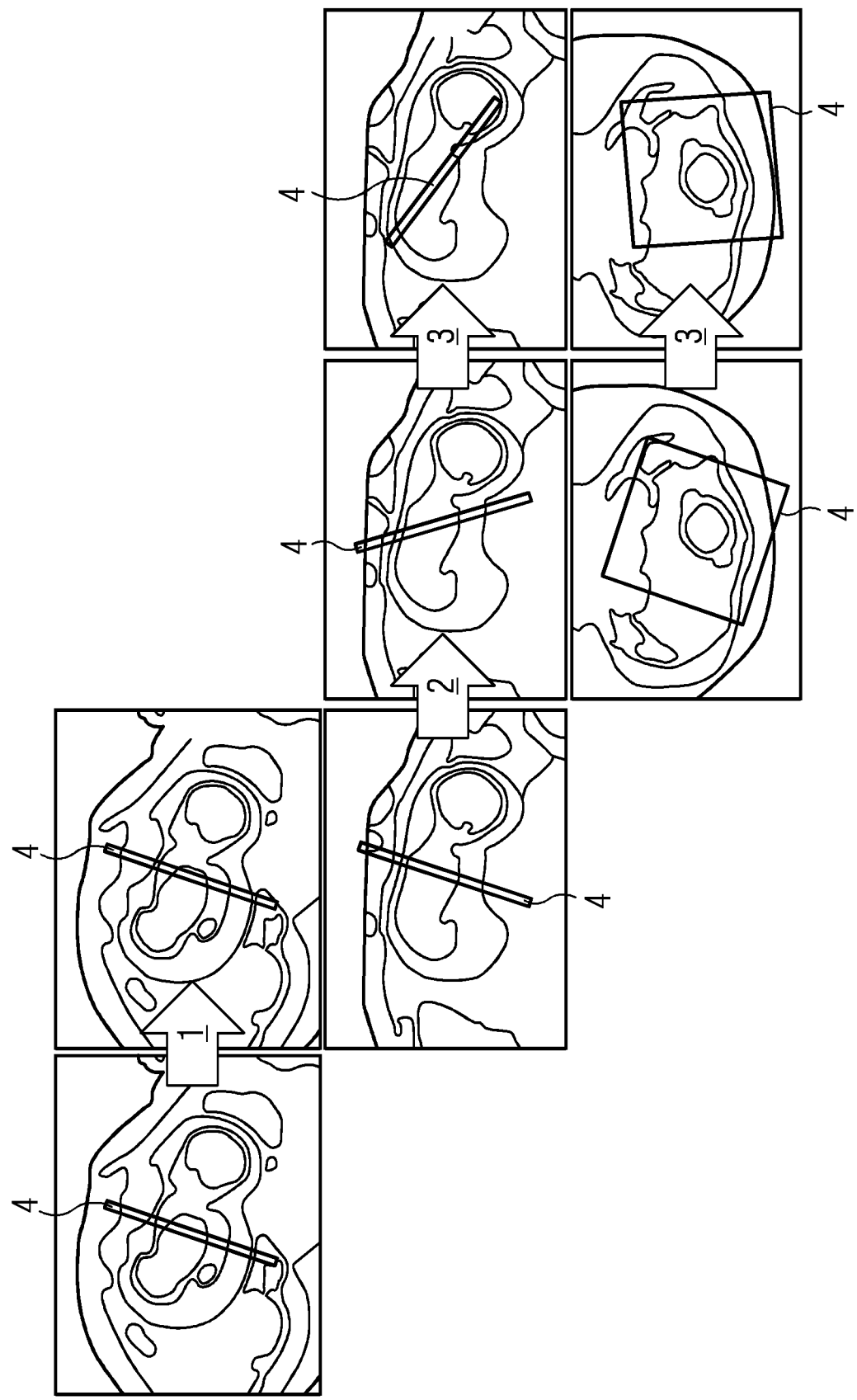

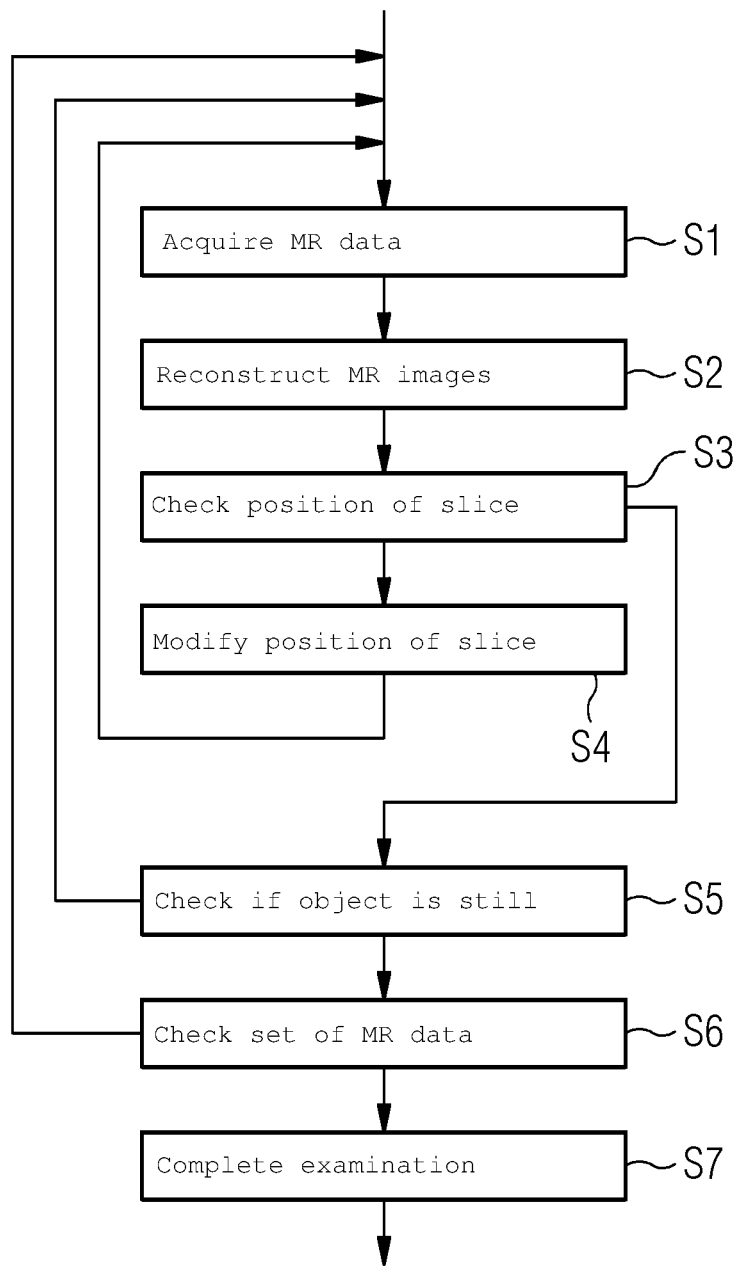

INTERACTIVE DATA ACQUISITION AND RECONSTRUCTION BY A MAGNETIC RESONANCE SYSTEM

The application claims the benefit of European Patent Application No. EP 17165537.6, filed Apr. 7, 2017, which is hereby incorporated by reference in its entirety.

TECHNICAL FIELD

The present disclosure relates to interactive data acquisition and reconstruction by a magnetic resonance (MR) system, in particular, in order to permit investigation of a fetal heart in utero.

BACKGROUND

Congenital heart disease occurs at a rate of roughly 4 to 13 cases per 1000 live births and is at present the most important cause of child mortality. Fetal echocardiography is at present the method of choice for identifying congenital heart disease, because the method is a safe, easy-to-perform, and inexpensive investigatory method with which images may be produced in real time and severe congenital heart disease reliably identified. Fetal echocardiography is, however, highly dependent on the investigating physician and is sometimes limited by acoustic windows, difficulties in imaging the distal vessel system, the position of the fetus, maternal obesity, or abdominal scarring from previous operations.

Because the previously described factors have virtually no impact on the quality of MR imaging, MR imaging is used in the second and third trimesters as a complementary investigatory method, if for example diagnosis by echocardiography is not unambiguous. MR imaging is, however, in principle based on the assumption that the object to be investigated does not move during data acquisition. More specifically, all the data collected during a single data acquisition may be spatially consistent with one another. The following requirements or problems accordingly arise for MR imaging of the fetal heart:

It is not possible to acquire an electrocardiogram (ECG) signal from the fetus in order to synchronize data acquisition with the fetal heartbeat, as is conventional when MR imaging an adult heart.

Due to the unpredictable and spontaneous movement of the fetus, the planning of data acquisition is very difficult. Such movements of the fetus are frequently only identified in the reconstructed images.

SUMMARY AND DESCRIPTION

The object of the present disclosure is to provide MR imaging of a fetal heart in which the previously described problems are solved.

The scope of the present disclosure is defined solely by the appended claims and is not affected to any degree by the statements within this description. The present embodiments may obviate one or more of the drawbacks or limitations in the related art.

For example, the object of the present disclosure is achieved by a method for interactive acquisition of data, by a magnetic resonance system, by a computer program product, and by an electronically readable data storage medium described herein.

The present disclosure provides a method for interactively acquiring MR data from an object under investigation by a magnetic resonance system. The method includes acquiring the MR data in a portion of the volume of the object under investigation with the magnetic resonance system.

The method also includes automatically reconstructing MR images based on the acquired MR data and displaying the MR images in real time. Displaying the MR images in real time here means that the MR images are displayed while data acquisition (e.g., for subsequent images) is still under way. For example, acquiring the data for a MR image may last for a time interval of 0.5 seconds (s) and reconstructing the MR image may last for a further 0.5 s, such that the MR images are displayed roughly 1 s after the start of data acquisition of the MR data for the respective MR image.

The method also includes determining a time interval, during which a predetermined condition in the displayed MR images is met. In this act, it is possible to check based on the displayed MR images whether the specified condition is maintained throughout the time interval. In this manner, it is advantageously also possible as it were indirectly to check whether the predetermined condition was met throughout the time interval during data acquisition.

The method also includes automatically reconstructing quality MR images based on the MR data acquired during the time interval. The temporal resolution of the quality MR images is here higher than the temporal resolution of the MR images which are displayed in real time. Automatic reconstruction of the quality MR images here in particular takes place offline because the quality MR images may not be displayed in real time. Furthermore, the spatial resolution of the quality MR images may also be higher than the spatial resolution of the MR images displayed in real time.

Checking, based on the MR images displayed in real time, whether the predetermined condition is met advantageously provides that this condition is also met for the MR data from which the quality MR images are reconstructed. Using the same MR data both for reconstructing the MR images displayed in real time and for reconstructing the quality MR images thus on the one hand has the advantage that the same MR data is used for reconstructing two different kinds of MR images. On the other hand, using the same MR data for the MR images and for the quality MR images has the advantage that it is possible to check based on the MR images displayed in real time that the predetermined condition is met for the MR data.

The object under investigation may be a heart of a living fetus located within the womb.

The present disclosure may thus advantageously be used instead of fetal echocardiography for investigating a congenital heart condition in a fetus.

The predetermined condition may be movement of the fetus within the time interval. In other words, according to this embodiment, the predetermined condition in the displayed MR images is met if no movement of the fetus is identified during this time interval.

This embodiment offers the advantage that it is provided based on the MR images displayed in real time that the fetus does not move within the predetermined time interval. As a result, it is in turn advantageously provided that reconstruction of the quality MR images is not negatively affected by movement of the fetus.

According to a further embodiment, the MR data is acquired by two-dimensional radial data acquisition in which the MR data is acquired along radially extending trajectories. The angle which occurs between two temporally directly successive radially extending trajectories here corresponds to the golden angle.

The golden angle may refer to the smaller golden angle that divides an angle of 180° in the golden section. It is, however, also possible to use the larger golden angle which divides the angle of 180° in the golden section and, together with the smaller golden angle, gives rise to 180°. Furthermore, it is also possible to use the smaller or larger golden angle which in each case divide a full circle (360°) in the golden section.

Selecting the angle between, in each case, two temporally successive radially extending trajectories according to the golden angle advantageously minimizes artifacts due to rapidly switching gradients (e.g., eddy-current artifacts).

According to one variant of the previously described embodiment, the MR data is acquired by the same set of radially extending trajectories being repeatedly acquired. The number of trajectories of this set here corresponds to a high number in the Fibonacci sequence (e.g., 987 or higher). In other words, the set of trajectories is acquired a first time, wherein the set of trajectories is then subsequently acquired a second time, etc.

The number of trajectories corresponding to a high number in the Fibonacci sequence provides that the angle of the final trajectory in the $n^{th}$ data acquisition of the set of trajectories is located fairly accurately at 0°. If the first trajectory in the $(n+1)^{th}$ data acquisition of the set of trajectories has the golden angle to a starting line located at 0°, the angle between the final trajectory of the $n^{th}$ data acquisition and the first trajectory of the $(n+1)^{th}$ data acquisition virtually corresponds to the golden angle.

By the number of trajectories thus corresponding to the high number in the Fibonacci sequence, the data acquisition corresponds to data acquisition in which each following trajectory in each case has the golden angle to the preceding trajectory, although data acquisition is subdivided into a plurality of portions, wherein in each portion the MR data is in each case acquired along the set of trajectories.

If the number of trajectories of the set for example corresponds to the number 6765 in the Fibonacci sequence, the MR data for 55 MR images may for example be acquired for each portion of the data acquisition, wherein the MR data for each MR image is acquired along 123 trajectories (55*123=6765).

It is, however, also possible for the data to be acquired by radial data acquisition, wherein the trajectories have a predetermined pseudo-random distribution. It is also possible to use predetermined pseudo-randomly distributed, spirally extending trajectories.

The (pseudo-)random distribution of the trajectories advantageously reduces artifacts in the reconstructed MR images and quality MR images.

Because the course of the trajectories is already known, the MR images and/or the quality MR images may be reconstructed based on parameters which are previously calculated (e.g., already available for data acquisition).

Because the trajectories and thus the K space points for which the MR data is acquired are already known beforehand, the corresponding parameters for reconstruction may likewise already be calculated beforehand. As a consequence, reconstruction of the MR images and/or the quality MR images may advantageously be accelerated.

Acquiring the MR data in a plurality of portions of in each case m trajectories, in each case spaced apart by the golden angle, wherein m in the number of m trajectories corresponds to a high number in the Fibonacci sequence, accordingly has the following advantages.

In one advantage, data acquisition corresponds as it were to pure data acquisition with the golden angle, in which each trajectory (apart from the first) has exactly the golden angle to its preceding trajectory.

In a second advantage, the parameters for reconstruction may nevertheless be precalculated in order to accelerate reconstruction.

The quality MR images may be reconstructed by carrying out a K-T sparse SENSE ("SENSivity Encoding") reconstruction. "K-T" here means that the MR data is acquired at different times ("T") in the K space ("K"). "Sparse" means that the K space is not completely, but instead only sparsely (e.g., incompletely), acquired during data acquisition.

In particular, reconstruction of the quality MR images includes, in one act, reconstructing intermediate MR images from the MR data. This reconstruction may be a direct K-T sparse SENSE reconstruction.

The reconstruction also includes, in an additional act, deriving information about the cardiac activity of the fetus from the intermediate MR images. In this act, information about the heartbeat of the fetus which corresponds to an ECG signal is automatically derived based on the intermediate MR images. The intermediate MR images have a lower image quality than the quality MR images. The image quality (e.g., the temporal resolution) of the intermediate MR images is, however, good enough in order to be able to derive the information about cardiac activity based on the intermediate MR images.

In an additional act, the quality MR images are reconstructed depending on the information about the cardiac activity of the fetus. Based on the information about cardiac activity, the heartbeat phase, in which the fetus' heart is located, may be derived at each point in time. By taking account of this information about the respective heartbeat phase during reconstruction of the quality MR images, it is advantageously possible to improve the quality of the quality MR images. A K-T sparse SENSE reconstruction, which is guided based on the information about the cardiac activity of the fetus, may also be used during reconstruction of the quality MR images.

Reconstruction based on the three acts outlined above may also be denoted as a three-stage reconstruction.

According to a further embodiment, the MR data is acquired in a slice within the object under investigation, such that the MR images reconstructed and displayed in real time correspond to representations of this slice. Based on these MR images, it is possible to check whether the position of the slice is suitable for the investigation to be carried out. When investigating fetal cardiac activity in utero, it is possible to check whether the slice is correctly arranged in the heart of the fetus. If such is not the case, the position of the slice may be modified depending on the MR images displayed in real time. To this end, the physician operating the magnetic resonance system may determine the manner in which the position of the slice is to be modified based on the displayed MR images and optionally based on further MR images generated with a localizer. Information for modifying the position of the slice is therefore acquired with the assistance of the MR images displayed in real time. Depending on this information, the position of the slice is correspondingly modified and the MR data for the slice (e.g., in the new position) is subsequently acquired.

This procedure (e.g., acquisition of MR data from the slice in its respective current position, displaying the reconstructed MR images in real time, checking the position of the slice, and modifying the position of the slice) may be carried out until the position of the slice is suitable for the investigation to be carried out.

This embodiment, for example, makes it possible for an operator (e.g., the physician operating the magnetic resonance system) to locate the fetus' heart, for example, based on localizer MR images in order then to arrange a slice, from which MR data is to be acquired, optimally with regard to the fetus' heart. Based on the MR images displayed in real time, the position of the slice may then be controlled and information or instructions from the operator for modifying this position may be acquired in order then to adjust the position of the slice depending on said information or instructions.

The present disclosure also provides a magnetic resonance system configured to interactively acquire data from an object under investigation. The magnetic resonance system includes a high frequency (HF) control unit (e.g., a HF controller or processor), a gradient control unit (e.g., a gradient controller or processor), and an image sequence controller (e.g., an image sequence controller or processor) designed to acquire data from the object under investigation. A computing unit (e.g., a computer or processor) of the magnetic resonance system is furthermore designed to reconstruct MR images in real time based on the MR data. A display unit (e.g., a display) of the magnetic resonance system is configured to display the reconstructed images. A time interval during which a specific condition is met in the images is defined with an input unit (or input device) of the magnetic resonance system. The computing unit is additionally designed to reconstruct quality MR images based on the MR data acquired within the time interval. The temporal resolution during reconstruction of the quality MR images is here higher than the temporal resolution during reconstruction of the MR images.

The advantages of the magnetic resonance system here substantially correspond to the advantages of the method, which have previously been explained in detail and are therefore not repeated here.

The present disclosure further describes a computer program product, in particular a computer program or an item of software, which may be loaded into a memory of a programmable controller or of a computing unit of a magnetic resonance system. All or various of the previously described embodiments of the method may be carried out with this computer program product when the computer program product is running in the controller or control device of the magnetic resonance system. The computer program product here possibly requires program code or functions, (e.g., libraries and auxiliary functions), in order to achieve the corresponding embodiments of the method. In other words, one of the above-described embodiments of the method may be carried out by the computer program product having the computer program code. The item of software may be source code (e.g., C++), which has yet to be compiled (e.g., translated) and bound or only needs to be interpreted, or executable software code which only needs to be loaded into the corresponding computing unit or control device for execution.

The present disclosure finally discloses an electronically readable data storage medium, (e.g., a DVD, magnetic tape, hard disk, or USB stick), on which electronically readable control information, in particular software (cf. above), is stored. When this control information (e.g., software) is read from the data storage medium and stored in a control device or computing unit of a magnetic resonance system, all the embodiments of the previously described method may be carried out.

BRIEF DESCRIPTION OF THE DRAWINGS

The present disclosure is hereinafter described in detail based on exemplary embodiments with reference to the appended figures.

FIG. 1 depicts a schematic diagram of an example of a magnetic resonance system with which MR data may be acquired interactively from an object under investigation.

FIG. 2 depicts diagrammatically how the position of a slice may be modified based on the MR images displayed in real time.

FIG. 3 depicts a flow diagram of one embodiment of the method.

DETAILED DESCRIPTION

FIG. 1 depicts a magnetic resonance system with which, as is explained below, MR data may be acquired from an object under investigation. The magnetic resonance system 10 includes a magnet 11 for generating a polarization field BO, wherein a person under investigation 13 arranged on a couch 12 is advanced into the magnet 11 in order to capture spatially encoded magnetic resonance signals from the person under investigation 13 and, in particular, from a fetal heart located in the person under investigation 13. The coils used for signal capture, (e.g., a whole-body coil or local coils), are not shown for reasons of clarity. The disclosure may be applied in "parallel imaging", in which the MR signals are simultaneously captured with a plurality of local coils or a coil array of local coils. The magnetization generated by the polarization field BO may be deflected from the equilibrium position and spatially encoded by applying high-frequency pulses and switching magnetic field gradients and the resultant magnetization is detected by the receive coils. The manner in which MR images may be produced by applying the HF pulses and switching magnetic field gradients in various combinations and sequences is known in principle to a person skilled in the art and is not explained in any greater detail here.

The magnetic resonance system 10 furthermore includes a control unit 20 that may be used for controlling the magnetic resonance system 10. The controller 20 includes a gradient control unit 15 for controlling and switching the necessary magnetic field gradients. A HF control unit 14 is provided for controlling and generating the HF pulses for deflecting the magnetization. An image sequence controller 16 controls the sequence of magnetic field gradients and HF pulses and thus indirectly controls the gradient control unit 15 and the HF control unit 14. An operator may control the magnetic resonance system and input information via an input unit 17, while MR images and other information required for control may be displayed on a display unit 18. A computing unit 19 with at least one processor unit (not shown) is provided for controlling the various units in the control unit 20. A memory unit 21 (e.g., a memory) is furthermore provided, in which program modules or programs may for example be stored, which, when executed on the computing unit 19 or the processor unit (e.g., processor) thereof, are capable of controlling running of the magnetic resonance system. The computing unit 19 is configured, as is explained below, to calculate the MR images and the quality MR images from the acquired MR data.

FIG. 2 depicts diagrammatically how the position of a slice in which MR data is to be acquired may be modified.

Based on overview images, an operator (e.g., a physician operating the magnetic resonance system) places a slice 4 in the desired portion of the volume of the object under investigation (e.g., in the heart of the fetus in utero). MR images (not shown), which are reconstructed based on the MR data acquired in the slice 4 and displayed in real time, enable the operator very quickly to check whether the position of the slice 4 is correct. If the operator is not satisfied with the current position of the slice, instructions or information may be acquired in order to modify the position depending on these instructions or this information.

FIG. 2 depicts possible changes in position of the slice. The image portions in FIG. 2 which are connected by the arrow labeled with reference sign 1 show a simple shift of the slice 4 without modification of the direction vector of the slice 4. In contrast, the image portions which are connected by the arrow labeled with reference sign 2 show a rotation of the slice 4, wherein the direction vector of the slice remains in the displayed plane. Finally, the image portions which are connected by the arrows labeled with reference sign 3 show a displacement of the slice 4 in which the slice 4 is both shifted and tilted.

As soon as the position of the slice 4 has been modified, for example, by one of the changes shown in FIG. 2, the next MR data is acquired for the respective current slice 4 and reconstructed in real time into a MR image which is displayed. As a result, the physician (e.g., user of the magnetic resonance system) receives immediate feedback as to whether the current position of the slice 4 matches his/her intention. If such is not the case, he/she may at any time once again modify or correct the position of the slice 4.

FIG. 3 depicts the flow diagram of one embodiment of the method.

MR data is acquired in act S1. Based on this MR data, MR images are reconstructed in act 2 in such a way that they are displayed in the same act S2 with a delay of less than the image refresh rate (thus as it were in real time).

In act S3, the physician (or user of the magnetic resonance system) checks based on the displayed MR images whether the position of the slice 4 matches his/her wishes (thus, for example, extends through the heart of the fetus). If such is not the case, the method branches to act S4, in which the physician modifies the position of the slice according to his/her intention, as is shown by way of example in FIG. 2. In this case, the method jumps back from act S4 to act S1.

If the physician is satisfied in act S3 with the current position of the slice 4, the method branches from act S3 to act S5. In act S5, the object is checked based on the displayed MR images of the slice 4 whether the object under investigation (e.g., the fetus) is sufficiently still. For the purposes of a fetal investigation, the mother is requested to hold her breath. If a troublesome movement of the object under investigation (e.g., fetus) is nevertheless identified based on the displayed MR images, the method jumps back to act S1. If, on the other hand, no troublesome movement of the object under investigation is identified from monitoring of the displayed MR images over a predetermined time interval, the method branches to act S6.

In act S6, it is checked whether the set of MR data is capable, for example, to investigate the heart of the fetus for a congenital disease. If such is the case, the method branches to act S7, wherein the examination is completed. Otherwise, the method returns back to act S1. Jumping back to act S1 provides that the method also passes once more through act S3, in which the position of the slice may be configured to a possible new position of the fetus.

The research was funded in part by the Faculté de Biologie et Médicine of the University of Lausanne and in part by the Swiss National Science Foundation for the promotion of scientific research, grant nos. 320030_143923 and 326030_150828.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for an interactive acquisition of data from an object under investigation by a magnetic resonance (MR) system, the method comprising:
   acquiring, by at least one processor of the MR system, the data from the object under investigation, wherein the object under investigation comprises a heart of a living fetus within a body of a mother of the living fetus;
   automatically reconstructing, by the at least one processor, and displaying MR images, by a display of the MR system, in real time, based on the acquired data;
   receiving, by the at least one processor from an input device of the MR system, a selected time interval from the reconstructed and displayed MR images in real time in which there is no movement of the living fetus throughout the selected time interval, wherein the selected time interval is provided by an operator via the input device based on an identification by the operator of no movement of the living fetus in the displayed MR images for the selected time interval; and
   automatically reconstructing, by the at least one processor, improved MR images based on the data acquired within the selected time interval,
   wherein a temporal resolution during reconstruction of the improved MR images is higher than a temporal resolution during reconstruction of the MR images in real time, and
   wherein the same data within only the selected time interval is used for both the reconstructing of the MR images in real time and the reconstructing of the improved MR images.

2. The method of claim 1, wherein the data is acquired by radial data acquisition, and
   wherein two temporally directly successively acquired radially extending trajectories, in each case, form an angle corresponding to a golden angle.

3. The method of claim 2, wherein a same predetermined set of radially extending trajectories are repeatedly acquired during the radial data acquisition, and
   wherein a number of trajectories of the set corresponds to a number in a Fibonacci sequence of 987 or higher.

4. The method of claim 3, wherein one or both of the MR images and the improved MR images are reconstructed based on parameters precalculated for the trajectories.

5. The method of claim 1, wherein the data is acquired by radial data acquisition, and
wherein the data is acquired based on predetermined trajectories having a pseudo-random distribution.

6. The method of claim 5, wherein one or both of the MR images and the improved MR images are reconstructed based on parameters precalculated for the predetermined trajectories.

7. The method of claim 1, wherein the improved MR images are automatically reconstructed by a K-T sparse sensitivity encoding reconstruction, wherein K-T refers to MR data acquired at different times (T) in k-space (K).

8. The method of claim 1, wherein the automatic reconstruction of the improved MR images comprises:
reconstructing intermediate images from the data;
deriving information about a cardiac activity of the fetus from the intermediate images; and
reconstructing the improved MR images depending on the derived information about the cardiac activity.

9. The method of cairn 1, wherein the acquiring of the data comprises:
acquiring data for a slice within the object under investigation;
checking a position of the slice by the images displayed in real time;
acquiring information for modifying the position of the slice depending on the images displayed in real time;
modifying the position of the slice depending on the information; and
acquiring the data from the slice in the modified position.

10. The method of claim 9, wherein the data k acquired by radial data acquisition, and
wherein two temporally directly successively acquired radially extending trajectories, in each case, form an angle corresponding to a golden angle.

11. The method of claim 10, wherein a same predetermined set of radially extending trajectories are repeatedly acquired during the radial data acquisition, and
wherein a number of trajectories of the set corresponds to a number in a Fibonacci sequence of 987 or higher.

12. The method of claim 11, wherein one or both of the MR images and the improved MR images are reconstructed based on parameters precalculated for the trajectories.

13. The method of claim 9, wherein the data is acquired by radial data acquisition, and
wherein the data is acquired based on predetermined trajectories having a pseudo-random distribution.

14. The method of claim 13, wherein one or both of the MR images and the improved MR images are reconstructed based on parameters precalculated for the predetermined trajectories.

15. The method of claim 9, wherein the automatic reconstruction of the improved MR images comprises:
reconstructing intermediate images from the data;
deriving information about a cardiac activity of the fetus from the intermediate images; and
reconstructing the improved MR images depending on the derived information about the cardiac activity.

16. A magnetic resonance system configured to interactively acquire data from an object under investigation, the magnetic resonance (MR) system comprising:
one or more processors configured to:
acquire the data from the object under investigation, wherein the object under investigation comprises a heart of a living fetus within a body of a mother of the living fetus;
reconstruct MR images in real time based on the data;
receive, via an input device of the MR system, a selected time interval from the reconstructed and displayed MR images in real time in which there is no movement of the living fetus throughout the selected time interval, wherein the selected time interval is provided by an operator via the input device based on an identification by the operator of no movement of the living fetus in the displayed MR images for the selected time interval; and
reconstruct improved MR images based on the data acquired within the selected time interval, wherein a temporal resolution during reconstruction of the improved MR images is higher than a temporal resolution during reconstruction of the MR images in real time, and wherein the same data within only the selected time interval is used for both the reconstruction of the MR images in real time and the reconstruction of the improved MR images; and
a display configured to display the reconstructed MR images in real time.

17. A method for an interactive acquisition of data from an object under investigation by a magnetic resonance (MR) system, the method comprising:
acquiring in a slice, by at least one processor of the MR system, the data from the object under investigation, wherein the object under investigation comprises a heart of a living fetus within a body of a mother of the living fetus;
automatically reconstructing, by the at least one processor, and displaying MR images, by a display of the MR system corresponding to representations of the slice based on the acquired data, wherein the MR images are displayed in real time with a delay of less than an image refresh rate;
checking a position of the slice by the MR images displayed in real time to determine whether the position of the slice extends through the heart of the living fetus;
modifying the position of the slice when the slice does not extend through the heart of the living fetus; and
repeating the acquiring of data, the reconstructing and the displaying of MR images, the checking of the position, and the modifying of the position until a modified slice extends through the heart of the living fetus;
checking, from the MR images displayed in real time for the slice extending through the heart of the living fetus, whether there is movement of the living fetus within a selected time interval of the MR images;
checking, from the MR images displayed in real time for the slice extending through the heart of the living fetus with no identified movement of the living fetus, whether a set of MR data for the MR images is sufficiently large to investigate the heart of the living fetus for a congenital disease; and
completing the interactive acquisition of data when the set of MR data for the MR images is sufficiently large for the investigation of the congenital disease.

18. The method of claim 17, further comprising:
repeating, when movement of the living fetus is identified in the MR images displayed in real time, the acquiring of data, the reconstructing and the displaying of the MR images, the checking of the position, the modifying of the position, and the checking of the movement until no movement is identified.

19. The method of claim 17, further comprising:

repeating, when the set of MR data for the MR images is determined to not be sufficiently large enough for the investigation of the congenital disease, the acquiring of data, the reconstructing and the displaying of the MR images, the checking of the position, the modifying of the position, the checking of the movement until no movement is identified, and the checking of whether the set of MR data for the MR images is sufficiently large.

* * * * *

UNITED STATES PATENT AND TRADEMARK OFFICE
CERTIFICATE OF CORRECTION

PATENT NO. : 11,147,455 B2
APPLICATION NO. : 15/944635
DATED : October 19, 2021
INVENTOR(S) : Jerome Chaptinel et al.

Page 1 of 1

It is certified that error appears in the above-identified patent and that said Letters Patent is hereby corrected as shown below:

In the Claims

Column 9, (Claim 10; Line 36):
"The method of claim 9, wherein the data k acquired by"
Should be replaced with:
"The method of claim 9, wherein the data is acquired by"

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*